United States Patent [19]

Tessier et al.

[11] Patent Number: 5,030,655

[45] Date of Patent: Jul. 9, 1991

[54] CYCLOPROPANE CARBOXYLATES

[75] Inventors: Jean Tessier, Vincennes; Jacques Demassey, Montevrain; Jean-Pierre Demoute, Auriol, all of France

[73] Assignee: Roussel Uclaf, Paris, France

[21] Appl. No.: 412,081

[22] Filed: Sep. 25, 1989

[30] Foreign Application Priority Data

Sep. 29, 1988 [FR] France .................. 88 12740

[51] Int. Cl.$^5$ ............... A01N 41/02; A01N 53/00; C07C 69/743; C07C 69/747
[52] U.S. Cl. ................... 514/521; 514/517; 514/519; 514/531; 514/553; 558/61; 558/407; 558/432; 558/434; 560/124; 562/125; 562/126
[58] Field of Search ........... 558/407, 61, 432, 434; 560/124; 514/531, 521, 519, 517, 553; 562/125, 126

[56] References Cited

U.S. PATENT DOCUMENTS

| | | | |
|---|---|---|---|
| 4,602,038 | 7/1986 | Tessier et al. | 558/407 X |
| 4,689,342 | 8/1987 | Tessier et al. | 558/407 |
| 4,925,874 | 5/1990 | Cadiergue et al. | 560/124 |

FOREIGN PATENT DOCUMENTS

| | | |
|---|---|---|
| 0187674 | 7/1986 | European Pat. Off. . |
| 0217342 | 4/1987 | European Pat. Off. . |
| 2099810A | 12/1982 | United Kingdom . |

Primary Examiner—Joseph Paul Brust
Attorney, Agent, or Firm—Bierman and Muserlian

[57] ABSTRACT

A compound selected from the group consisting of all possible isomeric forms and mixtures thereof of a compound of the formula $$R_1O-\overset{O}{\underset{\|}{S}}-\overset{X_1}{\underset{X_2}{\overset{|}{C}}}-CH-\overset{CH_3}{\underset{}{\overset{\ }{C}}}\overset{CH_3}{\underset{}{}}-CH-COOR_3 \quad \text{I}$$

wherein $R_1$ is selected from the group consisting of hydrogen, alkyl of 1 to 8 carbon atoms, alkenyl and alkynyl of 2 to 8 carbon atoms and cycloalkyl and cycloalkylalkyl of 3 to 8 carbon atoms, $R_2$ is selected from the group consisting of hydrogen, alkyl of 1 to 8 carbon atoms, alkenyl and alkynyl of 2 to 8 carbon atoms, cycloalkyl of 3 to 8 carbon atoms and acyl of 1 to 9 carbon atoms, $X_1$ and $X_2$ are individually selected from the group consisting of fluorine, chlorine, bromine, iodine, —$CF_3$, —CN, —COOR and

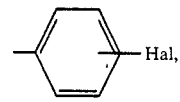

R is alkyl of 1 to 8 carbon atoms, Hal is chlorine, bromine or fluorine and $R_3$ is selected from the group consisting of hydrogen, alkyl of 1 to 8 carbon atoms and residue of an alcohol used in pyrethrinoid synthesis having excellent pesticidal properties.

27 Claims, No Drawings

CYCLOPROPANE CARBOXYLATES

STATE OF THE ART

Related prior art includes British Patent Application No. 2,099,810, European Patent Applications No. 0,187,674 and No. 0,217,342 and U.S. patent application Ser. No. 123,374 filed Nov. 20, 1987 now U.S. Pat. No. 4,925,874.

OBJECTS OF THE INVENTION

It is an object of the invention to provide all isomeric forms and mixtures thereof of the compounds of formula I and a process and novel intermediates for their preparation.

It is another object of the invention to provide novel pesticidal compositions and a novel method of combatting pests.

These and other objects and advantages of the invention will become obvious from the following detailed description.

THE INVENTION

The novel compounds of the invention are selected from the group consisting of all possible isomeric forms and mixtures thereof of a compound of the formula

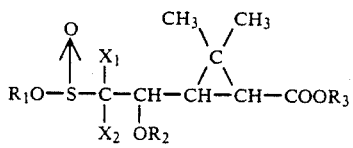

wherein $R_1$ is selected from the group consisting of hydrogen, alkyl of 1 to 8 carbon atoms, alkenyl and alkynyl of 2 to 8 carbon atoms and cycloalkyl and cycloalkylalkyl of 3 to 8 carbon atoms, $R_2$ is selected from the group consisting of hydrogen, alkyl of 1 to 8 carbon atoms, alkenyl and alkynyl of 2 to 8 carbon atoms, cycloalkyl of 3 to 8 carbon atoms and acyl of 1 to 9 carbon atoms, $X_1$ and $X_2$ are individually selected from the group consisting of fluorine, chlorine, bromine, iodine, $-CF_3$, $-CN$, $-COOR$ and

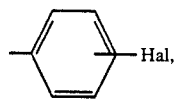

R is alkyl of 1 to 8 carbon atoms, Hal is chlorine, bromine or fluorine and $R_3$ is selected from the group consisting of hydrogen, alkyl of 1 to 8 carbon atoms and residue of an alcohol used in pyrethrinoid synthesis.

The compounds of formula I have several centers of asymmetry namely the carbons at position 1 and 3 of the cyclopropane, the carbon at position 1 and the sulfur of the lateral chain

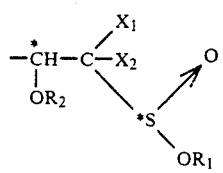

and may also have several centers of asymmetry in $R_3$. The invention includes the various stereoisomers possible as well as the mixtures of these stereoisomers.

When $R_1$ or $R_2$ are hydrocarbon, they are preferably methyl, ethyl, n-propyl, isopropyl, n-butyl, isobutyl, or tertbutyl; cyclopropyl, cyclobutyl, cyclopentyl or cyclohexyl; an alkyl having a cyclic group; a cyclopropyl, cyclobutyl, cyclopentyl or cyclohexyl substituted by at least one alkyl, for example 1-methylcyclobutyl, 1-methylcyclopentyl, 1-methylcyclohexyl or 2,2,3,3-tetramethylcyclopropyl; or vinyl or 1,1-dimethylallyl or an acetylene such as ethynyl or propynyl.

When $R_2$ is acyl, it is preferably $-COCH_3$, $-COC_2H_5$ $-COC_6H_5$ or $-COCH_2C_6H_5$. When $X_1$ and $X_2$ are $CO_2R$, R preferably is methyl, ethyl, n-propyl, isopropyl, n-butyl, isobutyl or tertbutyl. When $R_3$ is alkyl, it is preferably methyl, ethyl, n-propyl, isopropyl, butyl, isobutyl or tert-butyl.

Among the preferred compounds of formula I are those wherein $X_1$ and $X_2$ are both bromine, those wherein $R_1$ is hydrogen or methyl, those wherein $R_2$ is $-COCH_3$ or methyl and those wherein the cyclopropane coupla has the 1R,cis structure.

Among the preferred groups of $R_3$ are those selected from the group consisting of a) benzyl unsubstituted or substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, halogen and methylenedioxy,

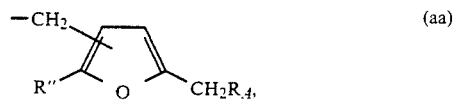

(aa)

R" is hydrogen or methyl, $R_4$ is monocyclic aryl or $-C\equiv CH$ particularly 5-benzyl-3-furyl-methyl,

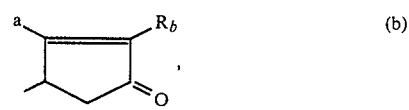

(b)

a is hydrogen or methyl, $R_b$ is aliphatic of 2 to 6 carbon atoms having at least one carbon atom unsaturation,

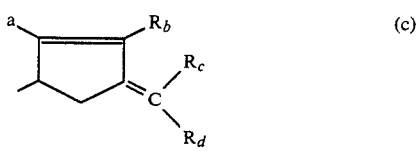

(c)

a and $R_b$ have the above definitions and $R_c$ and $R_d$ individually are selected from the group consisting of hydrogen, halogen, alkyl of 1 to 6 carbon atoms, aryl of 6 to 10 carbon atoms, cyano and alkoxycarbonyl of 2 to 5 carbon atoms,

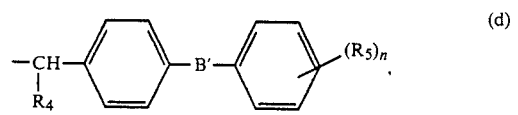

(d)

B' is selected from the group consisting of $-O-$, $-S-$,

—CH$_2$—, sulfone and sulfoxide, R$_4$ is selected from the group consisting of hydrogen, —CN, —CH$_3$,

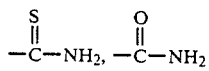

and —C≡CH, R$_5$ is selected from the group consisting of hydrogen, halogen and methyl, n is 0, 1 or 2,

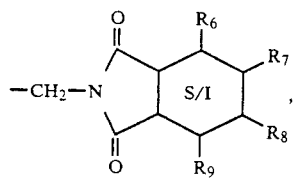  (e)

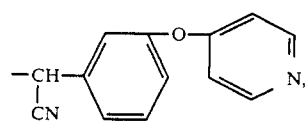  (f)

R$_6$, R$_7$, R$_8$ and R$_9$ are individually hydrogen, chlorine or methyl, S/I indicates an aromatic ring, dihydro ring or tetrahydro ring,

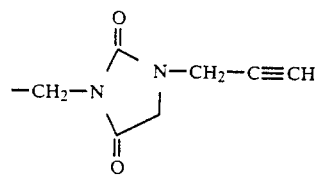  (g)

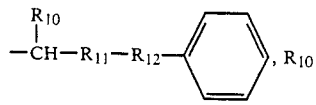  (h)

is hydrogen or cyano, R$_{12}$ is —CH$_2$— or —O—, R$_{11}$ is thiazolyl or thiadiazolyl and R$_{12}$ is linked to R$_{11}$ by the carbon atoms between the sulfur and nitrogen atoms,

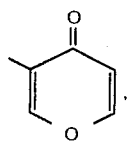  (i)

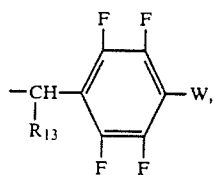  (j)

R$_{13}$ is hydrogen or cyano, W is selected from the group consisting of hydrogen, fluorine, —CH$_3$ and —OCH$_3$,

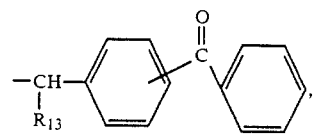  (k)

R$_{13}$ has the above definition and the benzyl is m- or p-,

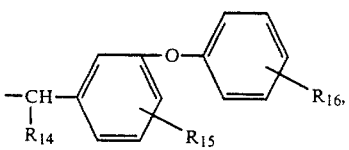  (l)

R$_{14}$ is selected from the group consisting of hydrogen, —CH$_3$, —CN and ethynyl, R$_{15}$ and R$_{16}$ are individually hydrogen, fluorine or bromine,

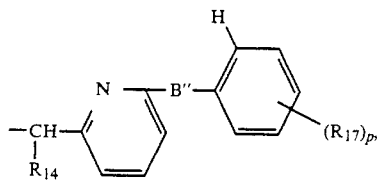  (m)

R$_{14}$ has the above definitions, the R$_{17}$s are individually selected from the group consisting of hydrogen, alkyl of 1 to 4 carbon atoms, alkylthio of 1 to 4 carbon atoms, alkylsulfonyl of 1 to 4 carbon atoms, —CF$_3$ chlorine, bromine, fluorine and methylenedioxy, p is 0, 1 or 2, B'' is —O— or —S—,

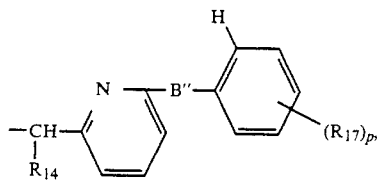  (n)

R$_{18}$ is selected from the group consisting of hydrogen, methyl, cyano and ethynyl, R$_{19}$ is different from R$_{18}$ and is hydrogen, fluorine or bromine, Ar is aryl of 6 to 14 carbon atoms,

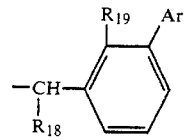  (o)

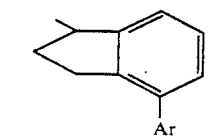  (p)

and A$_r$ is defined above.

Especially preferred for R$_3$ are —CH$_2$—CH=CH$_2$, —CH$_2$—CH=CH—CH$_3$, —CH$_2$—CH=CH—CH=CH$_2$, —CH$_2$—C≡CH and —CH$_2$—CH=CH—CH$_2$—CH$_3$. 3-phenoxy-benzyl, α-cyano-3-phenoxy-benzyl, α-ethynyl-3-phenoxy-benzyl, 3-benzoyl-benzyl, 1-(3-phenoxy-phenyl)-ethyl and α-thioamido-3-phenoxy-benzyl.

The novel process of the invention for the preparation of a compound of formula I comprises reacting a compound of the formula

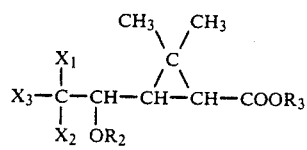

II wherein $X_1$, $X_2$, $R_2$ and $R_3$ have the above definitions and $X_3$ is chlorine, bromine or iodine with sodium dithionite in an aqueous media to obtain a compound of the formula

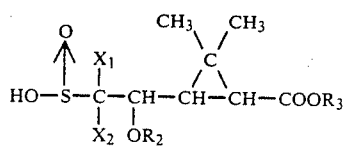

$I_A$ and optionally reacting the latter with an esterification agent capable of introducing $R_1'$ to obtain the compound of the formula

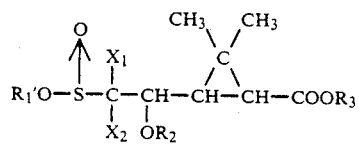

$I_B$ wherein $R_1'$ is $R_1$ other than hydrogen. Preferably, the compounds of formula II and sodium dithionite are reacted in the presence of water and a co-solvent such as methanol or tetrahydrofuran or dimethylformamide to dissolve the compound of formula II.

The compounds of formula II are novel and may be prepared according to the following reaction scheme

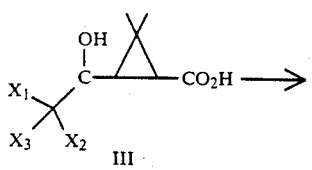

III

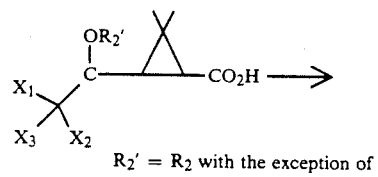

$R_2' = R_2$ with the exception of H

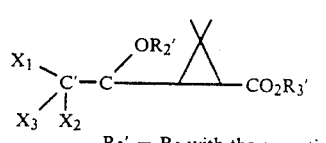

$R_3' = R_3$ with the exception of H

The compound of formula III can also be first esterified and then the free hydroxy can be functionalized by $R_2'$. The compound of formula III are generally known and may be prepared by the process of French Patent No. 2,396,006.

The novel pesticidal compositions of the invention are comprised of a pesticidally effective amount of at least one compound of formula I and an inert carrier. The compositions are useful to combat pests such as parasites of vegetables and of warm-blooded animals as well as parasites of premises and are particularly useful to combat insects, nematodes and parasitic acariens which attack warm-blooded animals and vegetables.

The compositions of the invention are particularly useful to combat insects in the agricultural field, for example, to control aphides and larvae of lepidoptera and coleoptera and are usually used at a dose of 10 to 300 g of the compounds of formula I per hectare. The compositions are also useful to combat insects in the premises for example to combat flies, mosquitoes and beetles.

The compounds of formula I possess an excellent lethal power and a very good knock-down power and have the advantages of being very photostable and not being toxic to mammals. The various properties of the compounds of formula I correspond perfectly to those required for modern agrochemical use permitting the protection of crops without damage to the environment.

The pesticidal compositions of the invention are useful to combat vegetable parasitic acariens and nematodes as well as to combat animal parasitic acariens such as ticks, especially ticks of *Boophilus* species, *Hyalomnia* species, *Amblyomnia* species and *Rhipicephalus* species and to combat all sorts of scabies such as sarcoptic scabies, psoroptic scabies and chorioptic scabies.

The invention also includes compositions intended to combat parasites of warm-blooded animals, parasites of premises and parasites of vegetables containing at least one compound of formula I. For the compositions intended for premises for agricutural use, the compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula I.

In an advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 95% by weight, preferably.

In the case of a serpentine insecticide, the inert support may be made, for example, of pyrethrum marc, Tabu powder (or *Machilus Thumbergii* leaf powder), powder of pyrethrum stems, cedar needle powder, sawdust such as pine sawdust, starch and powder of coconut shells. The active dose in this case is preferably 0.03 to 1% by weight.

The compositions of the invention for premises use may be prepared as a spraying oil containing the active ingredient and the oil may soak the wick of a lamp which is then subjected to combustion. The concentration of the compound of the invention in the oil is preferably 0.03 to 95% by weight.

The insecticidal compositions as well as the acaricidal and nematocidal compositions of the invention may also contain one or more other pesticides and are in the usual powder, granule, suspension, emulsion or solution form. For acaricide use, the compositions are preferably wettable powders for foliar spraying containing 1 to 80% of the active ingredient of liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2-propyl-4,5-methylene-dioxy-benzene (piperonyl butoxide) or N-(2-ethyl-heptyl)bicyclo-[2,2-1] 5-heptene-2,3-dicarboximide or piperonyl-bis-2-(2'-n-butoxy-ethoxy)-ethyl acetal (tropital).

When the compositions are to be used to combat parasitic acariens of animals, the active compounds of the invention are very often incorporated into alimentary compositions in association with a nutritive mixture adapted to the animal to be fed. The nutritive mixture will vary depending upon the specific animal but usually contains cereals, sugars, and grains, soybean press cake, peanuts and turnsole, meal of animal origin such as fish meal, synthetic amino acids, mineral salts, vitamins and antioxidants.

The compositions of the invention show an excellent general tolerance and are equally useful as medicaments for treating affections created by ticks and scabies. The compositions may be used in veterinary and human medicines. In human medicine, the compositions may be used to combat lice as well as prevent or treat scabies. The compositions may also be used as antihelmintics.

The said medicaments may be administered externally by vaporization, by shampoo, by painting or by bathing. For veterinary usage, the compositions may also be administered by painting the dorsal spine by the "pour on" method as well as being administered digestively or parenterally.

The compositions of the invention are also useful as biocides or to regulate growth.

Another feature of the invention are insecticidal, acaricidal or nematocidal associations containing as an active ingredient at least one compound of formula I and as a second active ingredient at least one pyrethrinoid ester selected from the group consisting of esters of allethrolones, of 3,4,5,6-tetrahydrophthalimido-methyl alcohol, of 5-benzyl-3-furylmethyl alcohol, of 3-phenoxy-benzyl alcohol and α-cyano-3-phenoxybenzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropyl-acetic acids, esters of allethrolone, 3,4,5,6-tetrahydrophthalimido-methyl alcohol, 5-benzyl-3-furyl-methyl alcohols, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of formula I and the above pyrethrinoid esters are in all possible stereoisomer forms.

The latter associated compositions of the invention are of particular interest for combatting by the polyvalence of their action, a large range of parasites or by manifesting a synergistic action in some cases.

The novel method of the invention for combatting parasites such as insects, nematodes and acariens comprises contacting the parasites with a pesticidally effective amount of at least one compound of formula I.

In the following examples there are described several preferred embodiments to illustrate the invention. However, it is to be understood that the invention is not intended to be limited to the specific embodiments.

EXAMPLE 1

α-cyano-3-phenoxy-benzyl [1R(1α((S*), 3α(R*))]-3-[1-acetyloxy-2,2-dibromo-2-methoxysulfinyl-ethyl]2,2-dimethyl-cyclopropane carboxylate

Step A: 1R cis 3-(2,2,2-tribromo-1R-acetoxyethyl)-2,2-dimethyl cyclopropane carboxylic acid A solution of 5.75 g of potassium tert-butylate, 20 ml of tetrahydrofuran and 30 ml of tert-butyl alcohol were added at −50° C. to a solution of 10 g of 1R cis 2,2-dimethyl-2-(1-hydroxy-2',2',2'-tribromoethyl)-cyclopropane carboxylic acid and 30 ml of tetrahydrofuran. After stirring for 30 minutes at −50° C., 2.4 ml of acetic anhydride were added. Stirring was continued while the temperature was allowed to rise to −20° C. After stirring for 50 hours at −20° C., the suspension was poured into 2N hydrochloric acid. Extraction was carried out with methylene chloride and the extracts were washed with water, dried and filtered. The filtrate was evaporated to dryness to obtain 9.7 g of a product which was poured into an aqueous solution of sodium bicarbonate. The reaction mixture was stirred for 16 hours at 20° C. and the crystallized product was separated and washed with water. The aqueous phase was acidified to a pH of 1 with hydrochloric acid and after extraction with methylene chloride, the extracts were washed with water, dried and filtered. The filtrate was evaporated to dryness to obtain 3.3 g of the desired product melting at 178° C.

Step B: α-cyano-3-phenoxy-benzyl 1R[1α(S*),3α(R*)]2,2-dimethyl-3-[1-acetyloxy-2,2,2-tribromethyl]-cyclopropane carboxylate 11.64 g of the acid of Step A and 6 g of (S) α-cyano-3-phenoxy-benzyl alcohol were dissolved in 75 ml of methylene chloride at +10° C. and a solution of 5.5 g of dicyclohexylcarbodiimide and 0.32 g of 4-dimethylamino-pyridine in 50 ml of methylene chloride was added. The temperature was returned to 20° C. and the mixture was stirred for 18 hours. The insoluble part was eliminated by filtration and the filtrate was concentrated under reduced pressure at 40° C. Chromatography was carried out on silica and elution with hexane-isopropyl ether mixture (7-3) yielded 13 g of the desired product.

Step C: 1α-cyano-3-phenoxy-benzyl [1R[1α(S*), 3α(R*)]]-3-[1-acetyloxy-2,2-dibromo-2-(methoxysulfinyl)-ethyl]-2,2-dimethylcyclopropane-carboxylate 2.5 g of sodium dithionite dissolved in 100 ml of water was added at about 20° C. to a solution of 7 g of the product of Step B in 100 ml of methanol and 120 ml of methanol and 50 ml of tetrahydrofuran were added. The reaction mixture was stirred for 30 minutes at 20° C. and the solvents were evaporated off under reduced pressure at 20°-25° C. The aqueous phase was acidified with a concentrated hydrochloric acid solution until a pH of 1.5 was obtained and the aqueous phase was saturated with sodium chloride and extracted with ethyl acetate. The extracts were dried and concentrated at 25° C. under reduced pressure. The residue was dissolved in 50 ml of methylene chloride and 80 ml of a solution of diazomethane in methylene chloride was added. The reaction mixture was then stirred for 15 minutes at 25° C. and concentrated. The crude product was purified by chromatography on silica and eluting with a hexane-isopropyl ether mixture (1-1) yielded. The following Diastereoisomer A $[\alpha]_D = -49°$ ±1° (c=1% in CHCl₃) and Diastereoisomer B $[\alpha]_D = +34.5°$ ±1% (c=1% in CHCl₃).

EXAMPLE 2

α-cyano-3-phenoxy-benzyl 1R[1α(S*),3α(R*)]-2,2-dimethyl-3-[1-acetyloxy-2,2-dibromo-2-(hydroxysulfinyl) ethyl]-cyclopropane carboxylate 2.96 g of the product of Step B of Example 1 were dissolved at about 5° C. in 30 ml of tetrahydrofuran, 10 ml of methanol and 10 ml of water, and a solution of 1 g of sodium dithionite in 10 ml of water was added. The temperature was allowed to rise to 20° C. and stirring was carried out for 45 minutes at this temperature. Most of the solvents were eliminated under reduced pressure at 20° C. After diluting with a little water, a solution was obtained which was extracted with ethyl ether. The aqueous phase was cooled to 0°±5° C., acidified with 14 mmoles of hydrochloric acid and extracted with ethyl ether. This new ethereal phase was dried, filtered and concentrated under reduced pressure at 20° C. to obtain 1.58 g of the desired product.

EXAMPLE 3

(3-phenoxy-benzyl 1R[1α, 3α(R*)]-2,2-dimethyl-3-[1-acetyloxy-2,2-dibromo-2-(hydroxysulfinyl)-ethyl]-cyclopropane carboxylate Step A: 3-phenoxy-benzyl 1R cis 3-(2,2,2-tribromo-1R-hydroxyethyl)-2,2-dimethyl cyclopropane carboxylate 10 g of 1R cis 2,2-dimethyl-2-(1-hydroxy-2', 2', 2'bromoethyl)-cyclopropane carboxylic acid were introduced at 20° C. into 200 ml of anhydrous benzene and the suspension was heated to reflux and distilled to carry away the water. At the end of distillation, the suspension was evaporated to dryness under reduced pressure and the residue was taken up in 40 ml of anhydrous dimethylformamide. The solution was cooled to -60° C. and 1.2 g of sodium hydride at 50% were added. The temperature was allowed to rise to 20° C., then stirring was carried out at 20° C. for 30 minutes. 5.4 g of metaphenoxybenzyl chloride were added and the reaction mixture was stirred at 20° C. for 48 hours. The suspension was poured into 2N hydrochloric acid and after stirring for 10 minutes, extraction was carried out with benzene. The extracts were washed with water, dried and filtered. The filtrate was evaporated to dryness under reduced pressure to obtain 14.5 g of product which was chromatographed on silica. Elution with a cyclohexane-ethyl acetate mixture (8-2) was effected and the product was crystallized from isopropyl ether and petroleum ether (B.p.=60°-80° C.) to obtain 10.35 g of the desired product melting at 50° C.

Step B: 3-phenoxy-benzyl 1R cis 3-(2,2,2-tribromo-1R-acetoxy-ethyl)-2,2-dimethyl-cyclopropane carboxylate A solution of 1 g of the product of Step A, 2 ml of anhydrous pyridine and 2 ml of acetic anhydride was stirred at 20° C. for 2 days and the solution was poured into 2N hydrochloric acid and stirred for one hour at 20° C. Extraction was carried out with benzene and the benzene solution was washed with water and dried, filtered and evaporated to dryness. The 0.782 g of crude product was chromatographed on silica and eluted with a cyclohexane-ethyl acetate mixture (9-1) to obtain the desired product.

Step C: 3-phenoxy-benzyl 1R [1α, 3α(R*)]-2,2-dimethyl-3-[1-acetyloxy-2,2-dibromo-2-(hydroxysulfinyl)-ethyl]-cyclopropane carboxylate 1.9 g of sodium dithionite in solution in 10 ml of water were added at 5° C. to a solution of 5.0 g of the product of Step B in Example 2 in a mixture of 80 ml of tetrahydrofuran and 20 ml of water. The temperature was allowed to rise to about 20° C. and the mixture was stirred for about 45 minutes at this temperature. The tetrahydrofuran was eliminated under reduced pressure at 20° C. and the residue was diluted with water to obtain a solution which was extracted with ethyl ether. The aqueous phase was decanted, acidified with 20 mmoles of hydrochloric acid and extracted with ethyl ether. The extracts were dried, filtered and concentrated to dryness under reduced pressure at 20° C. to obtain 3.08 g of the desired product.

EXAMPLE 4

3-phenoxy-benzyl 1R[1α, 3α(R*)]-2,2-dimethyl-3-[1-methoxy-2,2-dibromo-2-(hydroxysulfinyl)-ethyl]-cyclopropane carboxylate Step A: 1R cis 3-(2,2,2-tribromo-1R-methoxyethyl)-2,2-dimethyl cyclopropane carboxylic acid 5.75 g of potassium tertbutylate, 20 ml of tetahydrofuran and 30 ml of tertbutyl alcohol were added to a solution of 10 g of 1R cis 2,2-dimethyl-3-(1-hydroxy-2', 2', 2'-tribromoethyl)-cyclopropane carboxylic acid in 40 ml of tetrahydrofuran. The reaction mixture was stirred for 30 minutes at -20° C. and 2.5 ml of methyl sulfate and 10 ml of tetrahydrofuran were added. Stirring was continued for 17 hours at -20° C., and the resulting mixture was poured into a mixture of water and hydrochloric acid. After stirring for 10 minutes at 20° C., extraction was carried out with ethyl ether, and the organic phase was washed with water until a neutral pH was achieved. After drying, filtering and evaporating the filtrate to dryness under reduced pressure at 40° C., the product obtained was crystallized from benzene.

The crystals were separated, washed and dried to obtain 3.7 g of the desired product melting at 180° C.

Step B: 3-phenoxy-benzyl 1R[1α, 3α(R*)]-2,2-dimethyl-3-[1-methoxy-2,2-dibromo-2-(hydroxysulfinyl)-ethyl]-cyclopropane carboxylate 2.95 g of 1R cis 3-(2,2,2-tribromo-1R-methoxyethyl) -2,2-dimethyl cyclopropane carboxylic and 1.6 g of m-phenoxybenzyl alcohol were dissolved with magnetic stirring and under a nitrogen atmosphere in 50 ml of methylene chloride. 0.2 g of 4-dimethylamino-pyridine and 1.65 g of dicyclohexylcarbodiimide were added at 0°±5° C. The temperature was brought to 20° C. and stirring was carried out for 30 minutes. The insoluble part was eliminated by filtration and the filtrate was concentrated under reduced pressure at 40° C. Chromatography was carried out on silica and elution with a hexane-ethyl acetate mixture (95-5) to obtain 3.33 g of 3-phenoxy-benzyl) ester of the starting acid, which was dissolved in a mixture of 30 ml of tetrahydrofuran, 10 ml of methanol and 10 ml of water. 1.04 g of sodium dithionite in solution in 10 ml of water were then added at 0°±5° C. The temperature was allowed to rise to 20° C. and stirring was carried out for about 45 minutes at this temperature. The solvents were evaporated under reduced pressure at 20° C. and the residue was diluted with water, cooled to 0°±5° C., acidified to pH 1 by hydrochloric acid and extracted with ethyl acetate. The ethereal phase was dried, filtered and concentrated under reduced pressure at 20° C. to obtain 2.12 g of the desired product.

EXAMPLE 5

α-cyano-3-phenoxy-benzyl 1R[1α(S*), 3α(R*)]-2,2-dimethyl-3-[1-methoxy-2,2-dibromo-2-(hydroxysulfinyl)-ethyl]-cyclopropane carboxylate Step A: 1R[1α(S*), 3α(R*)]-2,2-dimethyl-3-(1-methoxy-2,2,2-tribromoethyl]-cyclopropane carboxylate 7.1 g of the acid prepared in Step A of Example 4 and 4.5 g of 1Sα-cyano-3-phenoxy-benzyl alcohol were dissolved in 100 ml of methylene chloride at 0±5° C. and 0.2 g of 4-dimethyl amino-pyridine and 4.1 g of dicyclohexyl carbodiimide were added. The temperature was returned to 20° C. and stirring was carried out for one hour. The insoluble part was eliminated by filtration and the filtrate was concentrated under reduced pressure at 40° C. Chromatography was carried out on silica and elution with a hexane-ethyl acetate mixture (9-1) yielded 10.32 g of the desired product.

Step B: α-cyano-3-phenoxy-benzyl 1R[1α(S*), 3α(R*)]-2,2-dimethyl -3-[1-methoxy-2,2-dibromo-2-(hydroxysulfinyl)-ethyl]-cyclopropane carboxylate 2.87 g of S α-cyano-3-phenoxy-benzyl 1R cis 2-(2,2,2-tribromo-1R-methoxyethyl)-2,2, -dimethyl cyclopropane carboxylate were dissolved with magnetic stirring in a solution of 25 ml of tetrahydrofuran, 20 ml of methanol and 10 ml of water. A solution of 0.94 g of sodium dithionite in 8 ml of water were added without exceeding 20° C. and the solution was stirred for 30 minutes at 20° C. The methanol and the tetrahydrofuran were eliminated under reduced pressure and the residue was diluted with water and extracted with ethyl ether. The aqueous phase was decanted, cooled to 0±5° C. and acidified with 10 mmoles of hydrochloric acid. Extraction was carried out with ethyl ether and the extracts were dried, filtered and concentrated under reduced pressure to obtain 2.35 g of the desired product.

EXAMPLE 6

α-cyano-3-phenoxy-benzyl 1R-[1α(S*), 3α(R*)]-2,2-dimethyl-3-(1-methoxy-2,2-dibromo-2-methoxysulfinyl-ethyl)-cyclopropane carboxylate 2.52 g of the product of Example 5 were dissolved in 20 ml of methylene chloride and a solution of diazomethane in methylene chloride was added at 0°±5° C. A drop of acetic acid was added and the solution was concentrated under reduced pressure at 20° C. Chromatography was carried out on silica and elution with 1,2-dichloroethane yielded 1.94 g of desired product.

EXAMPLE 7

PREPARATION OF A SOLUBLE CONCENTRATE

A homogenous mixture was made of 0.25 g of the product of Example 2, 1.0 g of piperonyl butoxide, 0.25 g of Tween 80 0.1 g of Topanol A and 98.4 g of water.

EXAMPLE 8

PREPARATION OF AN EMULSIFIABLE CONCENTRATE 0.015 g of the product of Example 3, 0.5 g of piperonyl butoxide 0.1 g Topanol A, 3.5 g of Tween 80 and 95.885 g of xylene were intimately admixed.

EXAMPLE 9

Preparation of an emulsifiable concentrate

A homogenous mixture is made of 1.5 g of the product of Example 4, 20.0 g of tween 80, 0.1 g of Topanol A and 78.4 g of xylene.

EXAMPLE 10

Preparation of a fumigant composition

The following are homogenously mixed 0.25 g of the product of Example 5, 25.00 g of tabu powder, 40.00 g of cedar leaf powder, 33.75 g of pine sawdust, 0.5 g of brilliant green and 0.5 g of p-nitrophenol.

BIOLOGICAL STUDY

1) Lethal Activity on the Household Fly

The insects tested were female household flies 4 to 5 days old and the test was carried out by topical spraying of 1 micro liter of acetone solution on the dorsal thorax of the insects using an Arnold micromanipulator. 50 flies were used per treatment and a mortality check was carried out 24 hours after treatment. The results obtained, expressed in LD 50 or dose in nanograms per individual needed to kill 50% of the insects, are as follows:

| Compound of Example | LD 50 ng/insect |
| --- | --- |
| 2 | 7.78 |
| 5 | 7.3 |

CONCLUSION

The products of the invention are endowed with a very good lethal effect on household flies.

2) Lethal Effect on *Spodoptera littoralis* Larvae

The tests were carried out by topical application of an acetone solution using an Arnold micromanipulator on the dorsal thorax of the larvae. 15 larvae per dose of the product tested were used and the larvae used were of the fourth larva stage, that is about 10 days old when they were bred at 24° C. and 65% relative humidity. After treatment, the individual larvae were placed on an artifical nutritive medium (Poitout medium) and the mortality check was carried out 48 hours after treatment. The experimental results obtained are summarized in the following table:

| Compound of Example | LD 50 ng/insect |
| --- | --- |
| 2 | 25.3 |
| 3 | 27.26 |
| 4 | 28.87 |
| 5 | 7.27 |

3) Lethal Effect on *Aphis cracivora*

Adults over 7 days old were used and 10 aphids per concentration used were used. A contact-ingestion method was used and treatment of a bean leaf was carried out with a Fisher gun, the leaf being placed in a plastic Petri dish on a wet paper disc. The treatment was carried out using 2 ml of acetone solution of the product tested (1 ml per side of leaf). Infestation by the insects was carried out after the leaf dried and the insects were kept in contact with the leaf for one hour, after which they were placed on untreated leaves and mortality was checked after 24 hours. The experimental results obtained are summarized in the following table:

| Compound of Example | LD 50 mg/liter |
| --- | --- |
| 3 | 3.6 |

Various modifications of the compounds and method of the invention may be made without departing from the spirit or scope thereof and it is to be understood that the invention is intended to be limited only as defined in the appended claims.

What is claimed is:

1. A compound selected from the group consisting of all possible isomeric forms and mixtures thereof of a compound of the formula

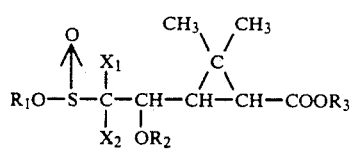

wherein $R_1$ is selected from the group consisting of hydrogen, alkyl of 1 to 8 carbon atoms, alkenyl and alkynyl of 2 to 8 carbon atoms and cycloalkyl and cycloalkylalkyl of 3 to 8 carbon atoms, $R_2$ is selected from the group consisting of hydrogen, alkyl of 1 to 8 carbon atoms, alkenyl and alkynyl of 2 to 8 carbon atoms, cycloalkyl of 3 to 8 carbon atoms and acyl of an organic carboxylic acid of 1 to 9 carbon atoms, $X_1$ and $X_2$ are individually selected from the group consisting of fluorine, chlorine, bromine, iodine, $-CF_3$, $-CN$ and $-COOR$, R is alkyl of 1 to 8 carbon atoms, and $R_3$ is selected from the group consisting of a) hydrogen, b) alkyl of 1 to 8 carbon atoms, c) benzyl unsubstituted or substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms and halogen

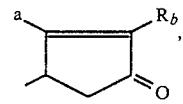

a is hydrogen or methyl, $R_b$ is aliphatic hydrocarbon of 2 to 6 carbon atoms having at least one carbon carbon unsaturation,

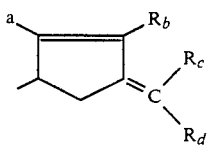

a and $R_b$ have the above definitions and $R_c$ and $R_d$ individually are selected from the group consisting of hydrogen, halogen, alkyl of 1 to 6 carbon atoms, carbocyclic aryl of 6 to 10 carbon atoms and cyano,

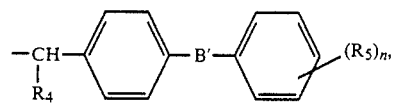

B' is selected from the group consisting of $-O-$, $-S-$,

$-CH_2-$, sulfone and sulfoxide, $R_4$ is selected from the group consisting of hydrogen, $-CN$, $-CH_3$,

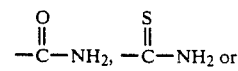

$-C\equiv CH$, $R_5$ is selected from the group consisting of hydrogen, halogen and methyl n is 0, 1 or 2,

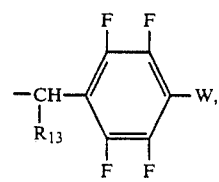

$R_{13}$ is hydrogen or cyano, W is selected from the group consisting of hydrogen, fluorine, $-CH_3$ and $-OCH_3$,

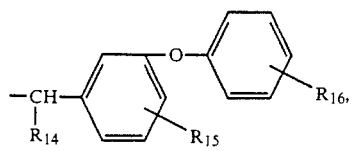
(h)

$R_{14}$ is selected from the group consisting of hydrogen, —CH$_3$, —CN and ethynyl, $R_{15}$ is fluorine or bromine and $R_{16}$ is hydrogen, fluorine or bromine

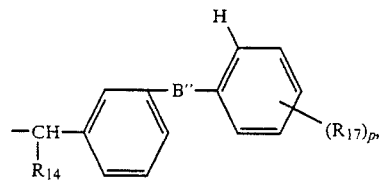
(i)

$R_{14}$ has the above definitions, $R_{17}$ are individually selected from the group consisting of hydrogen, alkyl of 1 to 4 carbon atoms, alkylthio of 1 to 4 carbon atoms, alkylsulfonyl of 1 to 4 carbon atoms, —CF$_3$, chlorine, bromine and fluorine and p is 1 or 2, B″ is —O— or —S—,

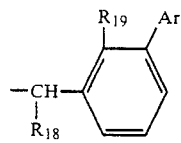
(j)

$R_{18}$ is selected from the group consisting of hydrogen, methyl, cyano and ethynyl $R_{19}$ is different from $R_{18}$ and is hydrogen, fluorine or bromine, Ar is carbocyclic aryl of 6 to 14 carbn atoms,

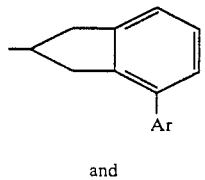
(k)

and

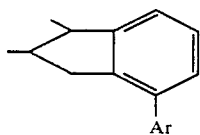
(l)

and Ar is carbocyclic aryl of 6 to 14 carbon atoms.

2. A compound of claim 1 wherein $X_1$ and $X_2$ are both bromine.

3. A compound of claim 1 wherein $R_1$ is hydrogen.
4. A compound of claim 1 wherein $R_1$ is methyl.
5. A compound of claim 1 wherein $R_2$ is —COCH$_3$.
6. A compound of claim 1 wherein $R_2$ is methyl.
7. A compound of claim 1 wherein the cyclopropane copula is of 1R cis structure.
8. A compound of claim 1 wherein $R_b$ is selected from the group consisting of —CH$_2$—CH=CH$_2$, —CH$_2$—CH=CH—CH$_3$, —CH$_2$—CH=CH—CH=CH$_2$, —CH$_2$—C≡CH, and —CH$_2$—CH=CH—CH$_2$—CH$_3$.
9. A compound of claim 1 wherein $R_3$ is selected from the group consisting of 3-phenoxy-benzyl, α-cyano-3-phenoxy-benzyl, α-ethynyl-3-phenoxy-benzyl, 3-benzoyl-benzyl, 1-(3-phenoxy-phenyl)-ethyl and α-thioamido-3-phenoxy-benzyl.
10. A compound of claim 1 wherein $R_3$ is α-cyano-3-phenoxy-benzyl.
11. A compound of claim 1 wherein $R_3$ is 3-phenoxy-benzyl.
12. An insecticidal composition comprising an insecticidally effective amount of at least one compound of claim 1 and an inert carrier.
13. A composition of claim 12 wherein $R_3$ is 3-phenoxy-benzyl or α-cyano-3-phenoxy-benzyl.
14. An animal feed containing an acaricidally effctive amount of at least one compound of claim 1.
15. A method of combatting ticks and mites comprising contacting ticks or mites with a tickicidally or miticidally effective amount of at least one compound of claim 1.
16. A method of combatting nematodes comprising contacting nematodes with a nematodicidally effective amount of at least one compound of claim 1.
17. A method of combatting insects comprising contacting insects with an insecticidally effective amount of at least one compound of claim 1.
18. A method of claim 17 wherein $X_1$ and $X_2$ are both bromine.
19. A method of claim 17 wherein $R_1$ is hydrogen.
20. A method of claim 17 wherein $R_1$ is methyl.
21. A method of claim 17 wherein $R_2$ is —COCH$_3$.
22. A method of claim 17 wherein $R_2$ is methyl.
23. A method of claim 17 wherein the cyclopropane portion is of 1R cis structure.
24. A method of claim 17 wherein $R_b$ is selected from the group consisting of —CH$_2$—CH=CH$_2$, —CH$_2$—CH=CH—CH$_3$, —CH$_2$—CH=CH—CH=CH$_2$, —CH$_2$—C≡CH and —CH$_2$—CH=CH—CH$_2$—CH$_3$.
25. A method of claim 17 wherein $R_3$ is selected from the group consisting of 3-phenoxy-benzyl, α-cyano-3-phenoxy-benzyl, α-ethynyl-3-phenoxy-benzyl, 3-benzoyl-benzyl, 1-(3-phenoxy-phenyl)-ethyl and α-thioamido-3-phenoxy-benzyl.
26. A method of claim 17 wherein $R_3$ is α-cyano-3-phenoxy-benzyl.
27. A method of claim 17 wherein $R_3$ is 3-phenoxy-benzyl.

* * * * *